(12) United States Patent
Segers et al.

(10) Patent No.: US 10,918,605 B2
(45) Date of Patent: Feb. 16, 2021

(54) PREPARATION OF SIZE-CONTROLLED MICROPARTICLES

(71) Applicant: BRACCO SUISSE SA, Cadempino (CH)

(72) Inventors: Tim Segers, Almelo (NL); Peter Frinking, Geneva (CH); Anne Lassus, Carouge (CH); Philippe Bussat, Pers-Jussy (FR); Emmanuel Gaud, La Croix-de-Rozon (CH); Samir Cherkaoui, Feigeres (FR)

(73) Assignee: Bracco Suisse SA, Cadempino (CH)

( * ) Notice: Subject to any disclaimer, the term of this patent is extended or adjusted under 35 U.S.C. 154(b) by 16 days.

(21) Appl. No.: 16/327,519

(22) PCT Filed: Aug. 30, 2017

(86) PCT No.: PCT/EP2017/071788
§ 371 (c)(1),
(2) Date: Feb. 22, 2019

(87) PCT Pub. No.: WO2018/041906
PCT Pub. Date: Mar. 8, 2018

(65) Prior Publication Data
US 2019/0175516 A1 Jun. 13, 2019

(30) Foreign Application Priority Data
Aug. 30, 2016 (EP) .................................... 16186356

(51) Int. Cl.
*A61K 9/50* (2006.01)
*A61K 9/00* (2006.01)
*A61K 9/127* (2006.01)

(52) U.S. Cl.
CPC .......... *A61K 9/5089* (2013.01); *A61K 9/0019* (2013.01); *A61K 9/127* (2013.01)

(58) Field of Classification Search
None
See application file for complete search history.

(56) References Cited

U.S. PATENT DOCUMENTS

2002/0159951 A1 10/2002 Unger et al.
2003/0003055 A1 1/2003 Unger et al.
2009/0274628 A1* 11/2009 Ottoboni .................. A61K 9/19
424/9.5

FOREIGN PATENT DOCUMENTS

WO 1995-16467 A1 6/1995
WO 2004-069284 A2 8/2004
WO 2013-141695 A1 9/2013

OTHER PUBLICATIONS

Castro-Hernandez, Elena et al., "Microbubble generation in a co-flow device operated in a new regime", Lab Chip, 2011, vol. 11, No. 12, pp. 2023-2029, The Royal Society of Chemistry.

(Continued)

*Primary Examiner* — Jeffrey D Washville
(74) *Attorney, Agent, or Firm* — Vivicar Law, PLLC

(57) ABSTRACT

A method for preparing a suspension of size-controlled microparticles stabilized by a layer of amphiphilic material. The method, which may be applied to preparations using microfluidic techniques, comprises controlling the temperature of the microparticles during the preparation process and preferably while collecting the formed microparticles.

15 Claims, 4 Drawing Sheets

(56) References Cited

OTHER PUBLICATIONS

Shin, Roger et al., "Flow-focusing regimes for accelerated production of monodisperse drug-loadable microbubbles toward clinical-scale applications", Lab Chip, 2013, vol. 13, pp. 4816-4826, The Royal Society of Chemistry.
Sorgi, Frank L. et al., "Large scale production of DC-Chol cationic liposomes by microfluidization", International Journal of Pharmaceutics, 1996, vol. 144, pp. 131-139, Elsevier Science BV.
Utada, Andrew S. et al., "Dripping to Jetting Transitions in Coflowing Liquid Streams", Physical Review Letters, Aug. 31, 2007, vol. 99, pp. 094502-1-094502-4, The American Physical Society.
Van Hoeve, Wim et al., "Microbubble formation and pinch-off scaling exponent in flow-focusing devices", Physics of Fluids, 2011, vol. 23, pp. 092001-1-092001-8, American Institute of Physica.
European Search Report for European application No. EP16186356.8, dated Feb. 9, 2017, 8 pages.
International Search Report and Written Opinion for PCT application No. PCT/EP2016/053960, dated Nov. 10, 2017, 14 pages.

* cited by examiner

PREPARATION OF SIZE-CONTROLLED MICROPARTICLES

CROSS-REFERENCE TO RELATED APPLICATIONS

This application is the national stage of corresponding international application number PCT/EP2017/071788, filed Aug. 30, 2017, which claims priority to and the benefit of European application no. EP16186356.8, filed Aug. 30, 2016, all of which are hereby incorporated by reference in their entirety.

TECHNICAL FIELD

The invention relates to a method for preparing size-controlled microparticles, such as gas-filled microvesicles, in particular by using a flow-focusing device.

BACKGROUND OF THE INVENTION

Gas-filled microvesicles are generally employed as suitable contrast agents in ultrasound imaging techniques, known as Contrast Enhanced Ultrasound (CEUS) Imaging. The gas of these microvesicles is typically entrapped or encapsulated in a stabilizing envelope comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles" in short).

Of particular interest are aqueous suspensions of gas-filled microvesicles where the bubbles of gas are bounded, at the gas/liquid interface, by a very thin envelope (film) involving a stabilizing amphiphilic material (typically a phospholipid) disposed at the gas to liquid interface. These suspensions are typically prepared by contacting powdered amphiphilic materials, e.g. freeze-dried preformed liposomes or freeze-dried or spray-dried lipid solutions, with air or any other gas, and then with an aqueous carrier, while agitating to generate a suspension of gas-filled microvesicles which can then be administered, preferably shortly after its preparation. The stabilizing layer may comprise, in addition to the above cited phospholipids, also other amphiphilic materials, such as fatty acids.

Ref. 1, discloses an alternative method for the production of gas-filled microvesicles which comprises emulsifying a hydrophobic liquid, typically an oil, in an aqueous dispersion of the amphiphilic material to obtain an emulsion of liquid filled microdroplets; the emulsion is then lyophilized and the lyophilized residue is subsequently reconstituted in the presence of a gas and an aqueous solvent to form the microbubble suspension.

Aqueous emulsions containing liquid filled microdroplets ("microdroplets" in short) can also be used as drug carriers. Either hydrophobic drugs or hydrophilic drug can be incorporated in a droplet coated by amphiphilic materials. In the first case, the amphiphilic material forms a monolayer around the droplet. In the second case, a double layer of amphiphilic material (liposome) is formed around an aqueous droplet. Microdroplets filled with a liquid with a relatively low boiling point $T_b$, e.g. perfluoropentane $T_b=29$ C, or with a (nano)emulsion of, e.g. drug containing nanodroplets in an oil with a low boiling point, have a great potential in drug delivery applications using ultrasound. Ultrasound can be used to trigger the vaporization of liquid droplets in in-vivo applications, thereby releasing their payload.

Conventional methods of preparation generally provide microvesicles or microdroplets (both identified herein as "microparticles") suspensions having a size distribution with a relatively high polydispersity index (PDI), mathematically defined as the ratio between the standard deviation "s" and the mean size "n" of the population of microparticles: PDI=s/n*100%. For instance, a typical preparation method may provide microparticles with a mean diameter of about 2-3 micrometer and a PDI of about 60%. Although microparticles, and particularly gas-filled microvesicles, with a relatively high PDI (such as 60%) are generally well suited for most of the actual imaging techniques, such PDI may nevertheless still be optimized for said imaging techniques. Moreover, for certain therapeutic ultrasound applications it is preferable to minimize the PDI.

Methods have thus been developed for preparing so-called "size-controlled" or "monodispersed" microparticles, i.e. gas-filled microvesicles or liquid filled microdroplets preparations where the PDI is lower than 10%, preferably lower than 5% and even more preferably lower than 2%.

Suitable methods for preparing monodisperse microparticles include, for instance, the use of microfluidic techniques, typically by using T-junctions or flow-focusing devices. In short, in a flow-focusing device, a flow of a first fluid component (e.g. a gas or an oil) is focused by a flow of a second fluid component through a narrow orifice. Typically the second fluid component is a liquid fluid comprising an envelope forming material (typically surfactants such as lipids, including phospholipids and/or fatty acids), which entraps the first fluid component to form the desired microparticles (in the form of gas-filled microvesicles or liquid droplets), which are stabilized against coalescence and dissolution by said envelope forming material.

The Applicant has however observed that, particularly under high flow rates (which are necessary for achieving high formation rates, e.g. $10^5$ microparticles per second or higher), the freshly formed microparticles may collide with a relatively high kinetic energy and such collisions may result in the coalescence of the microparticles. The consequences of such coalescence are that the dimensions of the formed microparticles may vary randomly, e.g. two, three and up to n-times the volume of the desired microparticles volume. Thus, the size and PDI of the microparticles population may become uncontrollable.

The Applicant has now found suitable preparation conditions which may be applied for limiting the coalescence of the microparticles prepared according to microfluidic methods.

In general terms, the Applicant has observed that by controlling the temperature close to the zone where the microparticles are formed, and particularly by subjecting the microparticles at a temperature around or above the transition temperature $(T_m)$ of the amphiphilic material(s) forming the stabilizing envelope of the microparticles, the coalescence phenomenon can be substantially reduced.

Furthermore, the Applicant has observed that a subsequent cooling of the formed suspension below the transition temperature of the amphiphilic materials may advantageously further help in maintaining the desired controlled size and PDI of the microparticles.

SUMMARY OF THE INVENTION

According to a first aspect, the present invention relates to a method for preparing a suspension of microparticles stabilized by a layer of amphiphilic material which comprises:

providing a first fluid flow and, separately, a liquid flow comprising said amphiphilic material;

directing said first fluid flow and said liquid flow through respective inlet channels towards a contact zone (where said respective flows come into contact);

directing said first fluid flow and said liquid flow from the contact zone through a calibrated orifice to obtain a suspension comprising said microparticles; and directing said suspension comprising said microparticles towards an outlet channel;

wherein an initial portion of said outlet channel is kept at a temperature (° C.) of not less than 20% lower with respect to the transition temperature of the amphiphilic material.

Preferably, the initial portion of the outlet channel is kept at a temperature (° C.) of not less than 10% lower with respect to the transition temperature of the amphiphilic material.

Said initial portion of the outlet channel preferably extends from the exit of the calibrated orifice until at least a zone where the flow of the aqueous suspension of microparticles reaches a substantially stationary velocity.

In a preferred embodiment, the suspension flows from the calibrated orifice to the outlet channel through a calibrated channel.

Depending on the geometry of the calibrated orifice (and channel) and of the outlet channel, said initial portion may extend for at least 0.1 mm from the exit of the calibrated orifice (or channel), preferably for at least 1 mm, more preferably for at least 2 mm. The length of said initial portion may be up to the total length of the outlet channel of the microfluidic device, e.g. 100 mm from the exit of the calibrated orifice.

According to preferred embodiments, said first fluid flow is a gas and said microparticles are gas-filled microvesicles.

Preferably, also the contact zone and the calibrated orifice are kept at the desired temperature. In such case, also the optional calibrated channel between the calibrated orifice and the outlet channel is preferably kept at said temperature.

According to another aspect of the invention, the obtained suspension is cooled down to a temperature below the transition temperature of the amphiphilic material within a relatively short period of time after the formation of the microparticles. For instance, the suspension is cooled within 10 seconds from the formation of the microparticles, preferably within 5 seconds and even more preferably within 2 seconds. Preferably, the suspension is cooled at a temperature (° C.) of at least 5% lower than $T_m$, more preferably at least 10% lower, down to e.g. 50% of $T_m$. In a preferred embodiment e.g. for amphiphilic materials with Tm higher than room temperature, the cooling temperature is room temperature (e.g. 22° C.), particularly when the microparticles suspension is stored at room temperature. In certain embodiments, the cooling temperature may also be lower, e.g. corresponding to the storage temperature when the suspension is stored at lower temperatures (e.g. 10° C.).

DETAILED DESCRIPTION OF THE INVENTION

Figure 1:
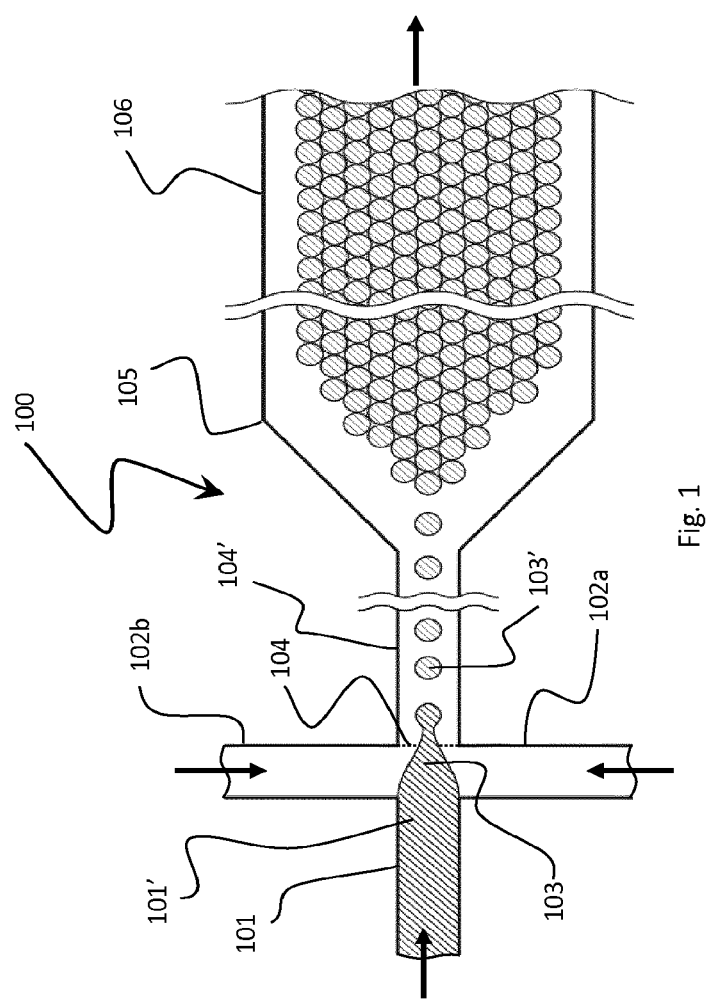
FIG. 1 is a schematic representation of the core portion of a flow-focusing device.

FIG. 1 shows a schematic representation of the core portion 100 of a flow-focusing device (chip) useful in the process of the invention. The chip comprises a first feed channel 101 for feeding a first fluid flow 101' and two additional feed channels 102a and 102b for supplying the liquid flow containing the amphiphilic material.

The first fluid flow (preferably a gas) and the two liquid flows are directed towards the contact zone 103 and then through the calibrated orifice 104, shown as a dotted line in FIG. 1.

As illustrated in FIG. 1, the calibrated orifice is connected to a calibrated channel 104' having preferably the same cross-section as the orifice, which is in turn connected to an initial portion 105 of the outlet channel 106. In an alternative embodiment (not shown) the calibrated orifice 104 may be a nozzle directly connected to the initial portion 105 of outlet channel 106 i.e. without the calibrated channel in-between.

The microparticles 103' are formed in the calibrated orifice and directed, through calibrated channel 104', to the initial portion 105 of the outlet channel 106. The hydraulic diameter of the outlet channel is generally larger than the hydraulic diameter of the calibrated orifice and typically increases from the initial diameter of the calibrated orifice to the final diameter of the outlet channel 106, corresponding substantially to the hydraulic diameter of a collecting tube (not shown), connecting the flow-focusing device to a container, e.g. a sealed vial.

As observed by the Applicant, due to the increase of the hydraulic diameter (and particularly at high manufacturing rates, e.g. about $10^5$ microparticles/s or higher), the velocity of the stream dramatically decreases from a relatively high velocity at the exit of the calibrated orifice down to the stationary state velocity of the suspension (that is typically reached downstream in the outlet channel and in the collection tube). This negative velocity gradient may cause the microparticles exiting from the calibrated orifice to collide onto microparticles flowing at a substantially lower velocity in the initial portion of the outlet channel. If the temperature of the microvesicles is not sufficiently high, these collisions may cause an uncontrolled collapse of the microparticles, with the result of undesirably increasing the polydispersity of the preparation.

As discovered by the Applicant, such undesired coalescence phenomenon may be substantially reduced by controlling the temperature of the microparticles in the initial portion 105 of the outlet channel of the device and preferably also in the contact zone 103 and in the calibrated orifice 104.

In particular, according to the invention, the initial portion of the outlet channel is preferably kept at a temperature of not less than 20% lower with respect to the $T_m$ of the amphiphilic material contained in the liquid flow and forming the stabilizing envelope of the microparticles. More preferably, said temperature is not less than 10% lower with respect to the $T_m$ of the amphiphilic material. While in general it is not necessary to have a temperature excessively higher than the $T_m$, such temperature may be as high as necessary, compatibly with the heat degradation resistance of the amphiphilic materials; for instance, the temperature may be up to 20% higher than the $T_m$ of the amphiphilic material, preferably up to 10% higher. In preferred embodiments, said temperature is at or slightly above (e.g. up to 5° C. higher) the $T_m$ of the amphiphilic material. The temperature control is particularly useful in the zone of the outlet channel where the flow of the aqueous suspension of microparticles has not yet reached a substantial stationary velocity, e.g. when the absolute velocity gradient is higher than about 10 s$^{-1}$. Depending on the geometry of the chip, said zone may extend for a length of from about 0.1 mm to 100 mm from the calibrated orifice, preferably from 1.0 to 50 mm and more preferably from 2.0 to 30 mm.

Advantageously, the temperature may similarly be controlled by applying the parameters specified above also to the contact zone and to the calibrated orifice (and, where present, to the calibrated channel).

As observed by the Applicant, the controlled temperature provides a substantial reduction of the coalescence among the formed microparticles.

The percentage of coalescence can be determined by calculating the total number of coalesced microparticles from the peaks of the size distribution from the images obtained with the optical microscope at the outlet channel of the flow-focusing device, e.g. by:

multiplying the total number of microparticles with a volume equal to two times the volume of the initially formed microparticles $V_i$ (second peak of the size distribution) by a factor two (since the coalesced microparticles originated from two microparticles); and adding this number to the total number of microparticles with three times the initial volume (third peak of the size distribution) multiplied by a factor three, and so on up to the $n^{th}$ peak in the measured size distribution.

The percentage of coalescence can thus be calculated by normalizing the total number of coalesced microparticles by the total number of produced microparticles, $$\text{coalescence \%} = \frac{\sum_{n=2}^{n} nN_{nVi}}{\sum_{n=1}^{n} nN_{nVi}} \times 100\%.$$

In general, a coalescence percentage of less than about 10%, preferably of less than about 5% and even more preferably of about 1% or less is desirable, down to coalescence percentages of e.g. 0.01%.

In addition, also the flow rate at which the device is operated may affect the coalescence of the microparticles. In particular, under the so-called "dripping" regime, as the velocity of the flows is relatively low (e.g. about 45 µL/min for a calibrated orifice of about 600 µm$^2$), and the microparticles size is typically larger (typically corresponding to the cross-section of the calibrated orifice), the coalescence phenomenon is relatively reduced. On the other side, under the so-called "jetting" regime, the increased velocity of the flow (e.g. 55 µL/min or higher for a calibrated orifice of about 600 µm$^2$), associated with the decreased microparticles size (typically, the faster the flow rate, the smaller the microparticles), determine an increase in the coalescence of the formed microparticles. However, while the formation rate of microparticles under the dripping regime is of about 10$^2$-10$^4$ microparticles per second, in the jetting regime such formation rate is increased to typically 10$^5$ microparticles per second or more. Thus, even if disadvantageous in terms of coalescence, high flow velocities are necessary for achieving acceptable formation rates of microparticles at the industrial scale (Ref. 2).

As shown in detail in the experimental part, by keeping the temperature at or around the $T_m$ of the amphiphilic material, a reduced coalescence is observed by using substantially lower concentrations of amphiphilic materials (as compared to the higher concentrations necessary where no heating is applied).

The flow-focusing device can be any of those known in the art, described for instance in (see e.g. Ref. 3). Preferably the flow focusing device comprises a chip, such as the one described e.g. in Ref. 4.

Figure 2:
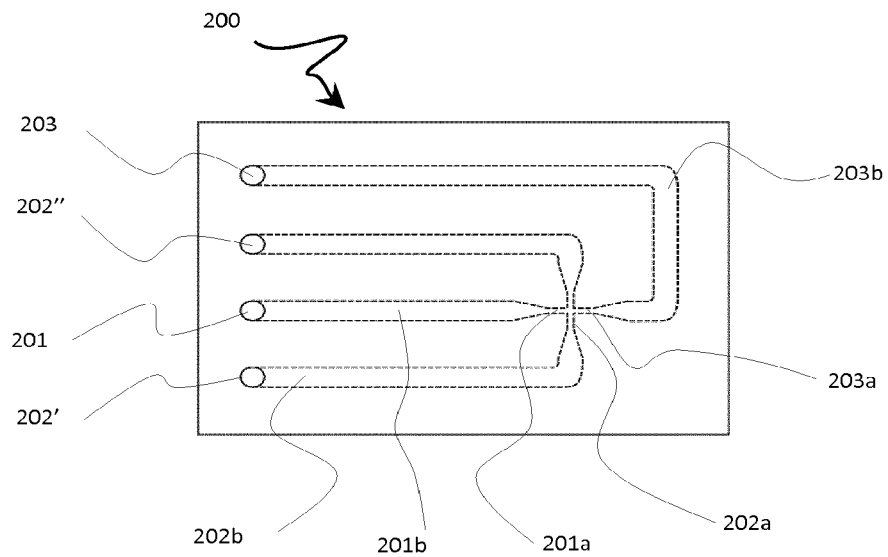
FIG. 2 shows an exemplary schematic representation (top view) of a chip useful for the flow-focusing process of the invention.

With reference to the schematic drawing of FIG. 2, the chip 200 may comprise a first inlet channel 201 through which the first fluid (preferably a gas) flow is supplied and two inlet channels 202' and 202" through which the liquid flow is supplied. Each of said inlet channels is connected to a respective reservoir through respective tubing (not shown). The chip further comprises an outlet channel 203 connected through a respective tubing to a container (not shown) adapted for collecting the suspension of microparticles. The cross-section of the final portion of the inlet channels 201a and 202a, close to the calibrated orifice, is substantially reduced with respect to the remainder of the channel 201b and 202b. The cross-section of this final portion 201a and 202a may vary from 25 to 1·10$^4$ µm$^2$, preferably from 200 to 1·10$^3$ µm$^2$, advantageously corresponding substantially to the cross-section of the calibrated orifice. The cross-section of the initial portions of the inlet channels may vary from 1·10$^3$ to 1·10$^6$ µm$^2$, preferably from 1·10$^4$ to 1·10$^5$ µm$^2$, while their length may vary from 50 mm to 1 mm, preferably from 2 mm to 5 mm. Similarly, the cross-section of the initial portion 203a of the outlet channel (corresponding to the calibrated channel in FIG. 1) is also relatively reduced; its section is generally calibrated according to the desired diameter of the microparticles to be prepared (see e.g. Ref. 4). For instance, for preparing monodispersed microparticles with a mean diameter of 5 µm, the calibrated orifice and the calibrated channel will have a cross-sectional area of about 250 to 2500 µm$^2$. Advantageously, the cross-sections of the inlet channels and that of the outlet channel are substantially the same, as well as that of their respective final and initial portions. The length of the calibrated channel 203a may vary from about 0.05 mm to about 10 mm, preferably from 1 mm to 5 mm, while the total length of the outlet channel may be up to 100 mm, preferably up to 50 mm and more preferably up to 30 mm. Typically, the chip is made out of two halves of quartz glass, fused silica, or any plastic (e.g. Poly(methyl methacrylate)) material. The channels can be produced by etching, either dry or wet, the internal surface of each half, for the whole desired depth and width. For instance, the surface may be etched at a constant depth of 14 µm and with a width of 15-20 µm for the respective calibrated portions close to the contact zone and a width of 0.5-1.0 mm for the remainder portions. Commercially available chips suitable for the use in the process of the invention are available for instance from Dolomite microfluidics (Royston, United Kingdom) or Micronit (Enschede, the Netherlands).

According to a preferred embodiment, in order to maintain the monodispersity of the formed microparticles, the suspension may then rapidly be cooled down to a temperature below the $T_m$ of the amphiphilic material, preferably once the flow of the suspension in the collection zone has reached a substantially stationary velocity.

Figure 3:
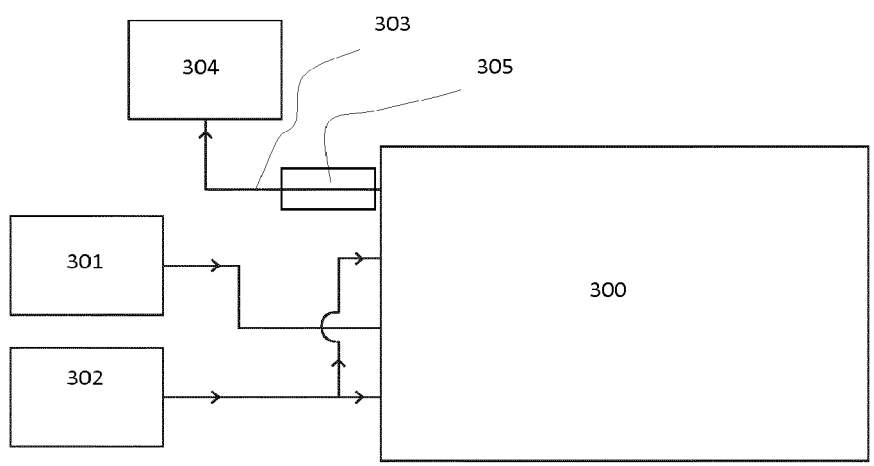
FIG. 3 shows an exemplary schematic drawing of a device useful for the process of the invention.

With reference to FIG. 3, a unit 300 (e.g. a chip as described in FIG. 2) comprising the core portion of a flow-focusing device may be kept at the desired temperature close or slightly above the $T_m$ of the amphiphilic material, as described above, e.g. by means of a thermostatic bath. The first fluid flow and the liquid flows comprising the amphiphilic material are supplied to unit 300 from respective reservoirs 301 and 302 to the unit 300 via respective supply tubing (with an internal diameter of e.g 100 to 1000 µm preferably from 150 to 250 µm). The outlet tubing 303 connects the outlet channel (not shown) of unit 300 (to a suitable collecting container 304, e.g. a sealed vial. As observed by the Applicant, it is advantageous to begin the cooling of the suspension of microparticles within few seconds from the formation of the microparticles, preferably as soon as the flow of the suspension reaches a substantially stationary velocity. Typically, said cooling may be initiated within 180 seconds from the formation of the microvesicles, preferably within 60 seconds, more preferably within 10 seconds and even more preferably within 2 seconds. Depending on the geometry of the flow-focusing device, the stationary flow is generally reached within few milliseconds or even less after the microparticles formation; the cooling may thus be applied starting from 1 milliseconds after the formation of the microparticles. As typically the suspension of microparticles reaches the exit of unit 300 within less than few milliseconds after formation, the cooling may advantageously be applied to the initial portion of the outlet tubing exiting the unit 300. Thus, an initial portion of the outlet tubing is advantageously subjected to cooling by suitable cooling means 305, e.g. a heat exchanger, in order to reduce the temperature of the suspension of gas-filled microparticles below $T_m$ of the amphiphilic material forming the stabilizing envelope of the microvesicles. The length of the initial portion of the outlet tubing subjected to the cooling may vary e.g. from 1 cm to 100 cm, preferably from 5 cm to 10 cm, depending, for instance from the heating temperature of the unit 300, the efficacy of the applied cooling, the contact time and so on.

Transition Temperature

When referring herein to the transition temperature ($T_m$) of an amphiphilic material, said temperature may be referred either to a single amphiphilic component or to a mixture of amphiphilic components.

In particular, when the amphiphilic material forming the stabilizing envelope is a mixture of different amphiphilic components, said $T_m$ is generally referred to as the $T_m$ of said mixture of amphiphilic components. For a mixture of amphiphilic materials, the measured $T_m$ generally corresponds to a molar ratio weighted mean of the $T_m$ of the individual components of the mixture.

The transition temperature $T_m$ of a lipid reflects a change in the physical state of the lipid from the ordered gel phase to the disordered liquid crystalline phase. In the gel phase, the hydrocarbon chains of the lipid are fully extended and closely packed. In the liquid phase, the hydrocarbon chains are randomly oriented and fluid like.

The $T_m$ of an aqueous lipid mixture may advantageously be measured by using differential scanning calorimetry (DSC). Calorimetric or thermal analysis allows for the measurement of heat flows related to transitions of a material as a function of time and temperature, and in a controlled atmosphere. DSC measures the difference of heat flow between a sample and an inert reference, by heating or cooling a sample at a constant rate in ° C./min. Measurements of $T_m$ of amphiphilic materials (pure or mixtures), including phospholipids, can be performed for instance by using a DSC-Q2000 device (TA Instruments, New Castle, Del. USA). Parameters such as the temperature at which the transition starts and reaches its peak and the enthalpy of the transition are measured to determine the $T_m$. Details of the measurements are provided in the experimental part.

Amphiphilic Materials

Suitable amphiphilic materials for use in a method of the invention comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol monoesters with fatty acids, including glycerol monopalmitate, glycerol monostearate, glycerol monomyristate or glycerol monolaurate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

According to a preferred embodiment, at least one of the compounds forming the envelope of the microparticles is a phospholipid, optionally in admixture with any of the other above cited materials. According to the present description, the term phospholipid is intended to encompass any amphiphilic phospholipid compound, the molecules of which are capable of forming a stabilizing film of material (typically in the form of a mono-molecular layer), particularly at the gas-water interface in the final microvesicles' suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipids are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoylphosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE and/or DSPE (including pegylated derivatives), DPPC, DSPC and/or DAPC with DSPS, DPPS, DSPA, DPPA, DSPG, DPPG, Ethyl-DSPC and/or Ethyl-DPPC.

For instance, a mixture of phospholipids may include phosphatidylcholine derivatives, phosphatidic acid derivatives and pegylated phosphatidylethanolamine, e.g. DSPC/DPPA/DPPE-PEG, DPPC/DPPA/DPPE-PEG, DSPC/DPPA/DSPE-PEG, DPPC/DPPA/DSPE-PEG, DAPC/DPPA/DPPE-PEG, DAPC/DPPA/DSPE-PEG, DSPC/DSPA/DPPE-PEG, DPPC/DSPA/DSPE-PEG, DSPC/DSPG/DPPE-PEG, DPPC/DSPG/DSPE-PEG.

According to an embodiment of the invention, the phospholipid is the main component of the stabilizing envelope of microvesicles, amounting to at least 50% (w/w) of the total amount of components forming the envelope of the gas-filled microvesicles, preferably at least 75%. In some of the preferred embodiments, substantially the totality of the envelope (i.e. at least 90% w/w) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids, e.g in proportions preferably ranging from zero to 50% by weight, more preferably up to 25%. For instance, mixtures of amphiphilic materials comprising phospholipids and fatty acids can advantageously be used, including DSPC/DPPG/palmitic acid, DSPC/DPPE-PEG/palmitic acid, DPPC/DPPE-PEG/palmitic acid, DSPC/DSPE-PEG/palmitic acid, DPPC/DSPE-PEG/palmitic acid, DSPC/DPPE-PEG/stearic acid, DPPC/DPPE-PEG/stearic acid, DSPC/DSPE-PEG/stearic acid or DPPC/DSPE-PEG/stearic acid.

The microparticles prepared according to the method of the invention may optionally comprise a targeting ligand.

The term "targeting ligand" includes within its meaning any compound, moiety or residue having, or being capable to promote, a targeting activity (e.g. including a selective binding) of the microparticles of a composition of the invention towards any biological or pathological site within a living body. Targets with which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

The targeting ligand may be an amphiphilic compound per se (which is admixed with the other components of the microvesicle) or a compound bound to an amphiphilic molecule (e.g. a phospholipid) employed for the formation of the microparticles.

In one preferred embodiment, the targeting ligand may be bound to an amphiphilic molecule (e.g. a phospholipid) forming the stabilizing envelope of the microparticles through a covalent bond. In order to covalently bind a desired targeting ligand, at least part of the amphiphilic compound forming the microparticles envelope shall thus contain a suitable reactive moiety and the targeting ligand containing the complementary functionality will be linked thereto according to known techniques, e.g. by adding it to a dispersion comprising the amphiphilic components of the microparticles. Preferably, the amphiphilic compound is a lipid bearing a hydrophilic polymer, such as those previously mentioned, preferably a pegylated phospholipid. In this case, the targeting ligand is linked to a suitable reactive moiety on the hydrophilic polymer. The amphiphilic compound may be combined with the desired targeting ligand before preparing the microvesicle, and the so obtained combination may be used for the preparation of the microvesicle. Alternatively, a microvesicle may first be manufactured, which comprises a compound (lipid or polymer-modified lipid) having a suitable moiety capable of interacting with a corresponding complementary moiety of a targeting ligand; thereafter, the desired targeting ligand is added to the microvesicle suspension, to bind to the corresponding complementary moiety on the microvesicle. According to an alternative embodiment, the targeting ligand may also be suitably associated with the microparticles via physical and/or electrostatic interactions.

Liquid Flow

The liquid used in the method of the invention comprises an amphiphilic material (as above defined) at a concentration of e.g. from 5.0 to 20 mg/mL, preferably from 7.5 to 15 mg/mL, preferably dispersed in an aqueous carrier.

Suitable aqueous carriers, which are preferably physiologically acceptable, comprise water (preferably sterile water), aqueous solutions such as saline (which may advantageously be balanced so that the final product for injection is not hypotonic), or solutions of one or more tonicity adjusting substances. Tonicity adjusting substances comprise salts or sugars, sugar alcohols, glycols or other non-ionic polyol materials (e.g. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethyl cellulose, hydroxyethyl starch or dextran.

In an alternative embodiment, particularly when the first fluid flow is a gas, an additional oil phase may be added for incorporating therapeutic hydrophobic substances into the microvesicles. To this end, two additional conduits may be provided in the device for supplying the desired oil phase, as described for instance by Ref. 5. The formed gas-filled microvesicles will thus have a film of oil disposed at the interface between gas and the stabilizing layer of amphiphilic material, which can be loaded with a desired therapeutic agent. Suitable oils may include any biocompatible oil which is liquid at room temperature including, for instance, mono-, di- or tri-esters of glycerol with saturated or unsaturated ($C_2$-$C_{15}$) alkyl chains (including homo- or hetero-allkylesters), such as glycerol monobutyrin, glycerol monolinoleate, 1,2-dihexanoyl glycerol, 1,2 dioctanoyl glycerol, 1,2-dioleyl-sn-glycerol, triacetin, tributyrin, tricaproin, tricaprylin, tricaprin, and mixtures thereof; or natural oils such as soya oil, olive oil, safflower seed oil, sunflower seed oil, peanut oil and mixtures thereof.

First Fluid Flow

According to a preferred embodiment, the first fluid flow is a gas or a precursor thereof.

In the process of the invention, any biocompatible gas, gas precursor or mixture thereof may be employed for the preparation of the microvesicles (hereinafter also identified as "microvesicle-forming gas").

The gas may comprise, for example, air; nitrogen; oxygen; carbon dioxide; hydrogen; nitrous oxide; a noble or inert gas such as helium, argon, xenon or krypton; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable gas-filled microvesicles suspensions.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutenes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{14}$.

It may also be advantageous to use a mixture of any of the above gases in any ratio. For instance, the mixture may comprise a conventional gas, such as nitrogen, air or carbon dioxide and a gas forming a stable microvesicle suspension, such as sulfur hexafluoride or a perfluorocarbon as indicated above. Examples of suitable gas mixtures can be found, for instance, in Ref. 6. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances, it may be desirable to include a precursor to a gaseous substance (i.e. a material that is capable of being converted to a gas in vivo). Preferably, the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and may be converted to a gas within the human body.

According to an alternative embodiment, the component of the first fluid flow may be a liquid.

In an embodiment, said liquid is substantially immiscible with water. Suitable liquids are for instance those listed in Ref. 1 including e.g. alkanes, such as branched or, preferably, linear ($C_5$-$C_{10}$) alkanes, e.g. pentane, hexane, heptane, octane, nonane, decane; alkenes, such as ($C_5$-$C_{10}$) alkenes, e.g. 1-pentene, 2-pentene, 1-octene; cyclo-alkanes, such as ($C_5$-$C_8$)-cycloalkanes optionally substituted with one or two methyl groups, e.g. cyclopentane, cyclohexane, cyclooctane, 1-methyl-cyclohexane; aromatic hydrocarbons, such as benzene and benzene derivatives substituted by one or two methyl or ethyl groups, e.g. benzene, toluene, ethylbenzene, 1,2-dimethylbenzene, 1,3-dimethylbenzene; alkyl ethers and ketones such as di-butyl ether and di-isopropylketone; halogenated hydrocarbons or ethers, such as chloroform, carbon tetrachloride, 2-chloro-1-(difluoromethoxy)-1,1,2-trifluoroethane (enflurane), 2-chloro-2-(difluoromethoxy)-1,1,1-trifluoroethane (isoflurane), tetrachloro-1,1-difluoroethane, and particularly perfluorinated hydrocarbons or ethers, such as perfluoropentane, perfluorohexane, perfluoroheptane, perfluoromethylcyclohexane, perfluorooctane, perfluorononane, perfluorobenzene and perfluorodecalin, methylperfluorobutylether, methylperfluoroisobutylether, ethylperfluorobutylether, ethylperfluoroisobutylether; and mixtures thereof.

Alternatively, said liquid may be a biocompatible oil including, for instance, esters of glycerol or natural oils as illustrated above.

Depending on the boiling temperature of the component of the first fluid flow, said component may go through different transition phases during the manufacturing process and/or subsequent storage of the suspension.

For instance, if the component has a relatively low boiling point (e.g. slightly above room temperature), it may be supplied as a liquid at room temperature, then transformed into a gas (or vapour) because of the heating above $T_m$, and subsequently again in a liquid in the final microparticles stored at room temperature. Alternatively, a liquid component may be heated above its boiling point (e.g. at or around the $T_m$), in order to supply it as a gas or vapour; upon cooling of the microparticles at room temperature, the component then condenses, thus providing the liquid-filled microdroplets.

According to an embodiment, the resulting suspension of calibrated liquid-filled microdroplets may go under a subsequent lyophilization process, in order to obtain a lyophilized cake which can then be stored in a vial under an atmosphere of a gas (such as those illustrated above), as described for instance in Ref. 1. The cake can then be reconstituted with a suitable aqueous liquid by gentle agitation to obtain a suspension of gas-filled microvesicles. In this case a lyoprotective agent (e.g. one of those illustrated in Ref. 1) may be added to the suspension, either directly to the liquid flow or to the formed aqueous suspension of microdroplets.

Use

The microparticles prepared according to the method of the invention may be used in a variety of diagnostic and/or therapeutic techniques, including in particular Ultrasound and Magnetic Resonance.

Diagnostic techniques include any method where the use of the gas-filled microvesicles allows enhancing the visualisation of a portion or of a part of an animal (including humans) body, including imaging for preclinical and clinical research purposes. A variety of imaging techniques may be employed in ultrasound applications, for example including fundamental and harmonic B-mode imaging, amplitude modulation, pulse or phase inversion imaging and fundamental and harmonic Doppler imaging; if desired three-dimensional imaging techniques may be used.

Microvesicles for diagnostic use may be administered (e.g. by injection) at a concentration of from about 0.01 to about 1.0 µL of gas per kg of patient, depending e.g. on their respective composition, the tissue or organ to be imaged and/or the chosen imaging technique. This general concentration range may of course vary depending on specific imaging applications, e.g. when signals can be observed at very low doses such as in amplitude modulation and pulse inversion imaging.

Possible other diagnostic imaging applications include scintigraphy, light imaging, and X-ray imaging, including X-ray phase contrast imaging.

Therapeutic techniques include any method of treatment (as above defined) of a patient which comprises the use of microparticles either as such (e.g. ultrasound mediated treatment ischemic strokes, clot lysis etc.) or in combination with a therapeutic agent (e.g. for the delivery of a bioactive compound to a selected site or tissue, such as in gene therapy or in the use as vaccine), and which is capable of exerting or responsible to exert a biological effect in vitro and/or in vivo, either by itself or upon specific activation by various physical methods (including e.g. ultrasound mediated delivery).

Microvesicles for therapeutic treatments may typically be administered in a concentration of from about 0.01 to about 5.0 µL of gas per kg of patient, depending e.g. from their respective composition, the type of subject under treatment, the tissue or organ to be treated and/or the therapeutic method applied.

The following examples will help to further illustrate the invention.

EXAMPLES

Materials

| | | |
|---|---|---|
| DPPC | dipalmitoyl-phosphatidylcholine | (1) |
| DSPC | distearoyl-phosphatidylcholine | (1) |
| DPPA | dipalmitoyl phosphatidic acid | (1) |
| DPPE-PEG5000 | Dipalmitoylphosphatidylethanolamine-polyethyleneglycol5000 | (1) |

(1) CordenPharma International, Plankstadt, Germany

Example 1

Preparation of Aqueous Dispersions of Amphiphilic Material

Two mixtures of amphiphilic materials with different phase transition temperatures ($T_m$) were used:
M1: DSPC:DPPA:DPPE-PEG5000 ($T_m$=55° C.)
M2: DPPC:DPPA:DPPE-PEG5000 ($T_m$=44° C.)
both in a molar ratio of 8:1:1.

The materials were added with the above molar ratios at a concentration of 20 mg/mL to a 2:1 (volume ratio) chloroform/methanol mixture under stirring at 60° C. until complete dissolution the amphiphilic material. The solvent was then evaporated under reduced pressure and the obtained film was dried overnight under reduced pressure. The dried material was then redispersed (at concentrations of from 5 to 15 mg/mL, as detailed in the part "preparation of microvesicles") in a mixture of glycerol, propylene glycol, and water (GPW, volume ratio of 5:5:90) at 60° C. under stirring for 30 minutes. TRIS buffer (20 mM) was added to adjust the pH value at 7. The dispersion was then sonicated by using a tip sonicator (Branson Sonifier 250) to homogenously disperse the material. The preparations were then filtered using a polycarbonate filter (0.45 µm pore size), cooled down to room temperature and degassed.

Measurement of Transition Temperature

Transition temperatures of amphiphilic materials (pure DPPC or DSPC and mixtures of DPPC:DPPA:DPPE-PEG5000 or DSPC:DPPA:DPPE-PEG5000) were determined by using commercial Differential Scanning calorimetry DSC-Q2000, with Tzero aluminum crucibles (TA Instruments, New Castle, Del. USA). System calibration, including temperature and heat flow, was carried out with Indium metal (enthalpy of fusion 28.71 J/g±0.5 J/g; onset temperature of fusion 156.6° C.±0.25° C.).

Dispersions of the amphiphilic material (pure or mixtures) in GPW/TRIS were prepared according to the procedure described above for the DSC measurements (about 30 µL each, concentration 10 mg/mL).

DSC measurements were carried out by heating at a constant temperature rate of 2° C./min over a temperature range from 20° C. to 80° C. Nitrogen was used as purging gas at a flow rate of 50 mL/min.

The results are illustrated in the table below:

| | Starting transition temperature (° C.) | Transition peak $T_m$ (° C.) |
|---|---|---|
| DPPC | 40 | 42 |
| DSPC | 52 | 55 |
| DPPC/DPPA/DPPE-PEG5000 | 41 | 44 |
| DSPC/DPPA/DPPE-PEG5000 | 52 | 55 |

Example 2

Preparation of Gas-Filled Microvesicles

Microvesicles were synthesized using a commercially available microfluidic flow-focusing device (Dolomite microfluidics, small droplet chip, 14 µm etch depth, part no. 3200136), mounted in a commercially available chip holder (Dolomite microfluidics, part numbers: 3000024, 3000109, 3000021) allowing for the leak tight connection of the chip to the gas and liquid supply tubing (Peek Upchurch, 1/16 inch O.D, 150 µm I.D.). The microvesicles formation channel had a width of 17 µm and a length of 135 µm. The overall channel depth was 14 µm. The chip and its holder were positioned in an optically transparent temperature controlled water bath that was mounted on an inverted microscope equipped with a 20 times magnification objective (Olympus, LMPLAN 20x) and a CCD camera (Lumenera, LM156M). The liquid co-flow rate was controlled using a syringe pump (Harvard PHD4400). The gas ($SF_6$) was pressure controlled using a pressure regulator (Omega, PRG101-25) connected to a pressure sensor (Omega, DPG1000B-30G). Individual microvesicles were automatically detected from the recorded optical images to measure their sizes offline on a PC using Matlab software (The Mathworks Inc., Natick, Mass.). Two different liquid co-flow rates were tested (45 µL/min or 55 µL/min) to operate the flow-focusing device under the dripping regime or under the more preferred jetting regime, respectively.

The microvesicle suspension was collected in a sealed vial and stored at room temperature.

Effects of Heating the Formed Microvesicles

FIGS. 4a to 4e show the results obtained using a liquid co-flow of the DSPC/DPPA/DPPE-PEG5000 suspension ($T_m$ 55° C.) as prepared above, with concentrations of amphiphilic material ranging from 5 to 15 mg/mL (FIG. 4a-4e, respectively) and at different temperatures of the thermostatic bath containing the microfluidic chip (similar to the one illustrated in FIG. 2). Squares (■) indicate experiments conducted under the dripping regime, while triangles (▲) indicate experiments conducted under the more preferred jetting regime.

Figure 4:
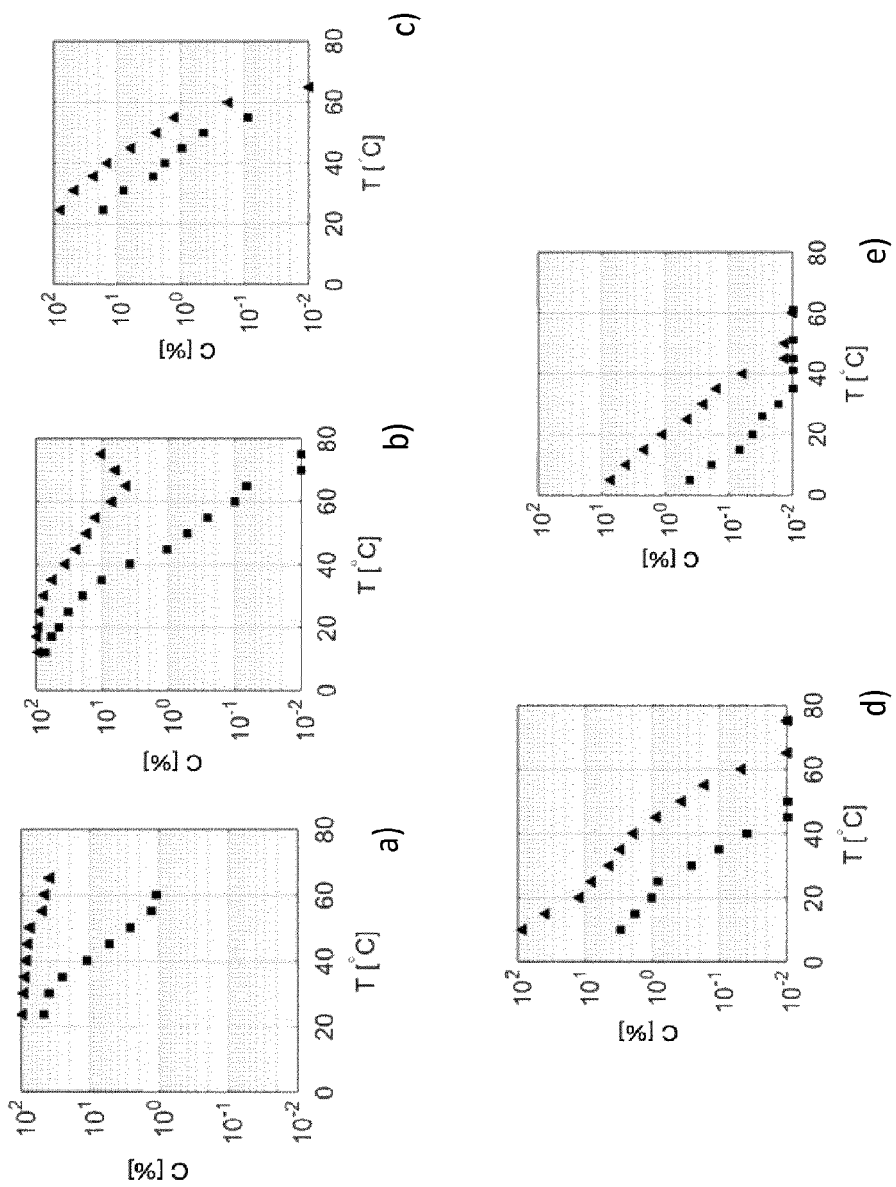
FIG. 4 illustrates experimental results of the temperature control during the formation of gas-filled microvesicles according to the invention.

As can be observed in these figures, the percentage of coalescence (C [%]) of microvesicles is generally lower in the dripping regime compared to the jetting regime. In addition, under both dripping and jetting regimes, the advantageous effect of reducing coalescence by increasing the temperature is apparent. Considering in particular the jetting regime, for concentrations of 7.5 mg/mL (FIG. 4b) increasing the temperature to the $T_m$ of the amphiphilic mixture (55° C.), or higher, results in a coalescence of microvesicles of about 10% or lower. Still focusing on the jetting regime, the same heating to or above the $T_m$ of the amphiphilic material provides a coalescence of less than 1% for concentrations of the amphiphilic material of 10 mg/mL (FIG. 4c). By increasing the concentration of the amphiphilic material to 15 mg/mL (FIG. 4e), similar results can be obtained at room temperature. Note that in this case the concentration of the amphiphilic material needs to be increased by 50%.

These results thus demonstrate that by keeping the temperature around the $T_m$ of the amphiphilic material, a reduction of the coalescence effect can be obtained (as compared to higher coalescence measured for the same preparation at lower temperatures). The results further show that by keeping the temperature around the $T_m$ of the amphiphilic material, similar percentages of coalescence may be obtained by using substantially lower concentrations of amphiphilic materials (as compared to the higher concentrations needed if no heating is applied).

Figure 5:
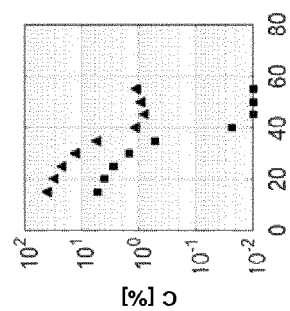
FIG. 5 illustrates experimental results of the temperature control during the formation of gas-filled microvesicles with other amphiphilic materials according to the invention.

FIG. 5 shows the results obtained using a liquid co-flow of the DPPC/DPPA/DPPE-PEG5000 suspension ($T_m$ 44° C.) as prepared above, with concentrations of amphiphilic material of 10 mg/mL at different temperatures of the thermostatic bath. Similarly, to the results discussed above, also in this case a coalescence of 1% or less is obtained when heating to a temperature close or higher than the $T_m$ of the amphiphilic material.

Effects of Downstream Cooling the Suspension

To evaluate the effects of downstream cooling on the dispersity of the microvesicles, different cooling conditions were tested.

According to setup A (early-cooled suspension), the suspension was passed through a heat exchanger (at 20° C.) 3 ms after microvesicle formation, to suddenly reduce the temperature of the suspension below $T_m$, particularly at room temperature. Accordingly, the tubing exiting from the chip in the thermostatic bath was passed through a heat exchanger after approximately 0.5 mm from the chip's exit.

According to setup B (late-cooled suspension), the suspension was passed through the same heat exchanger only 3 minutes after microvesicle formation. Accordingly, in this second configuration, the tubing exiting from the chip was replaced by a tubing with an inner diameter of 1 mm and this tubing was kept in the thermostatic bath for a length of approximately 20 cm and then passed through a heat exchanger.

Figure 6:
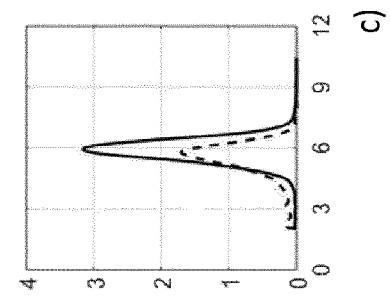
FIG. 6 illustrates experimental results of the cooling effect on a suspension of gas-filled microvesicles.
Figure 6:
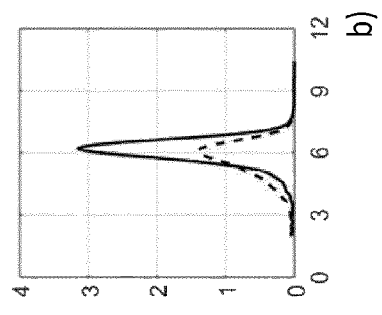
Figure 6:
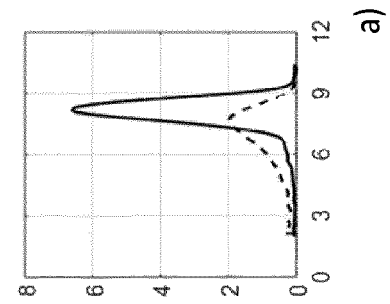

Both setups were tested at flow rates of 55, 65 and 75 μL/min and the results are illustrated in FIGS. 6a, 6b and 6c, respectively (X axis=diameter in mm, Y axis=relative count of microvesicles by number). In FIGS. 6a-6c, the dashed lines show the size distributions of late-cooled preparations, while solid lines show the size distributions of early-cooled preparations. It is apparent from these figures that the PDI of the early-cooled suspension is lower compared to the one of the corresponding late-cooled suspension. Moreover, it can be appreciated from these figures that the mean size of the microvesicles decrease with increasing flow velocity.

Similar results may be obtained with other mixtures of amphiphilic materials, particularly those combinations of amphiphilic materials previously illustrated.

CITED REFERENCES (1) WO 04/069284
(2) Utada, A. S et al., "*Dripping to jetting transitions in co-flowing liquid streams*", Phys. Rev. Lett. 2007, 99, 094502
(3) Intl. Pat. Appl. WO 2013/141695
(4) Castro-Hernandez, E. et al., "*Microbubble generation in a co-flow device operated in a new regime*", Lab. Chip. 2011, 11 (12), 2023-9
(5) R. Shih et al., "*Flow-focusing regimes for accelerated production of monodisperse drug-loadable microbubbles toward clinical-scale applications*", Lab. Chip 13, 4816-4826 (2013)
(6) Intl. Pat. Appl. WO 95/16467

The invention claimed is:

1. A method for preparing a suspension of liquid- or gas-filled microparticles stabilized by a layer of an amphiphilic material with a transition temperature, comprising:
   providing a first fluid flow and, separately, a liquid flow comprising the amphiphilic material;
   directing the first fluid flow through a first inlet channel and the liquid flow through a second inlet channel towards a contact zone;
   directing the first fluid flow and the liquid flow from the contact zone through a calibrated orifice to obtain the suspension of liquid- or gas-filled microparticles; and
   directing the suspension of liquid- or gas-filled microparticles towards an outlet channel;
   wherein an initial portion of the outlet channel is kept at a controlled temperature (° C.) of not less than 20% lower with respect to the transition temperature of the amphiphilic material.

2. The method according to claim 1, wherein the controlled temperature (° C.) is of not less than 10% lower with respect to the transition temperature of the amphiphilic material.

3. The method according to claim 1, wherein the initial portion of the outlet channel extends for a length sufficient for the suspension of liquid- or gas-filled microparticles to reach a substantially stationary velocity in the outlet channel.

4. The method according to claim 3, wherein the initial portion of the outlet channel extends from 0.1 mm to 100 mm from the calibrated orifice.

5. The method according to claim 3, wherein the initial portion of the outlet channel extends from 1 mm to 50 mm from the calibrated orifice.

6. The method according to claim 3, wherein the initial portion of the outlet channel extends from 2 mm to 30 mm from the calibrated orifice.

7. The method according to claim 1, wherein the contact zone and the calibrated orifice are also kept at the controlled temperature.

8. The method according to claim 1, further comprising subsequently cooling the suspension of liquid- or gas-filled microparticles at a cooling temperature below the transition temperature of the amphiphilic material.

9. The method according to claim 8, wherein the cooling is initiated within 60 seconds from the formation of the microparticles.

10. The method according to claim 8, wherein the cooling is initiated within 5 seconds from the formation of the microparticles.

11. The method according to claim 8, wherein the cooling temperature (° C.) is at least 5% lower than the transition temperature of the amphiphilic material.

12. The method according to claim 11, wherein the cooling temperature (° C.) is at least 10% lower than the transition temperature of the amphiphilic material.

13. The method according to claim 1, wherein the amphiphilic material comprises a phospholipid.

14. The method according to claim 1, wherein the first fluid flow is a gas and the microparticles are gas-filled microvesicles.

15. The method according to claim 14, wherein the gas comprises a biocompatible fluorinated gas or a precursor thereof.

* * * * *